United States Patent [19]

Basi

[11] Patent Number: 5,216,132
[45] Date of Patent: Jun. 1, 1993

[54] SOLUBLE T-CELL ANTIGEN RECEPTOR CHIMERIC ANTIGENS

[75] Inventor: Guriqbal S. Basi, Palo Alto, Calif.

[73] Assignee: Protein Design Labs, Inc., Mountain View, Calif.

[21] Appl. No.: 463,743

[22] Filed: Jan. 12, 1990

[51] Int. Cl.$^5$ .................. C07K 15/28; A61K 39/385; C12P 21/02

[52] U.S. Cl. .............................. 530/387.3; 530/402; 530/403; 424/88; 435/69.7

[58] Field of Search ............. 530/387, 389, 402, 403, 530/387.3, 388.75; 424/88; 435/69.7

[56] References Cited

U.S. PATENT DOCUMENTS

| | | | |
|---|---|---|---|
| 4,886,743 | 12/1989 | Hood et al. | 530/388.75 |
| 4,923,799 | 5/1990 | Mak | 530/388.75 |
| 5,116,964 | 5/1992 | Capon et al. | 435/252.3 |

OTHER PUBLICATIONS

Mariuzza et al., *Journal of Biological Chemistry* 264: 7310-7316, May 5, 1989.
Gascoigne et al., Proc. Natl. Acad. Sci. 84: 2936-2940, May 1987.
Becker et al., *Cell 58:* 911-921, Sep. 8, 1989.

*Primary Examiner*—Robert A. Wax
*Assistant Examiner*—Stephen Walsh

[57] ABSTRACT

Soluble antigens useful for efficient production of antibodies against human T-cell receptor epitopes are provided. A preferred antigen is a chimeric polypeptide comprising at least 100 amino acids from a V$\beta$ domain with solubility conferred by an immunoglobulin heavy chain CH2 or CH3 domain fused thereto. Product antibodies and methods for diagnostic and therapeutic uses for both antigens and antibodies are provided.

6 Claims, 4 Drawing Sheets

```
                    β8.1 LEADER PEPTIDE                              Vβ8.1
                 ┌─────────────────────────┐          ┌──────────────────────────────┐
                 -21                                    1          5         10        15
PREDICTED
β8.1 SEQUENCE:   M D S W T F C C V S L C I L L V A K H T D A   G V I Q S P R H E V T E M G E
                                                               * * * * * * * * * * * * * * *
                                                               * * * * * * * * * * * * * * *
SEQUENCE OF PROTEIN AFFINITY PURIFIED FROM TISSUE CULTURE SUPERNATANT: (G) V I Q S P R H (E) V T (T) M (G) 0

YIELD PER RESIDUE (P MOLES):                                   122 130
```

FIG. 5.

SOLUBLE T-CELL ANTIGEN RECEPTOR CHIMERIC ANTIGENS

FIELD OF THE INVENTION

This invention relates generally to the construction of fused gene segments using recombinant DNA techniques to produce T-cell receptor chimeric antigens in secretable form and, more particularly, to improved methods for producing antibodies specifically reactive with T-cell receptor epitopes.

BACKGROUND OF THE INVENTION

The vertebrate immune system is characterized by its ability to respond to an enormously diverse set of antigenic determinants, or epitopes. This response is effected through T and B lymphocytes, commonly referred to as T cells and B cells. The immune system, comprising these specialized cells, recognizes and processes foreign pathogens and macromolecules, typically clearing them from the body. Lymphocytes individually exhibit high specificity in recognition of particular molecular shapes and collectively exhibit great diversity in reacting with, i.e., specifically binding, a broad range of molecular structures. These properties are mediated through both T-cell receptors and immunoglobulins that serve as antigen receptors.

T cells usually recognize only antigens that are present on the surfaces of other cells. This recognition event generally occurs only when the antigens are correctly presented in combination with polymorphic cell surface molecules encoded by the major histocompatibility complex (MHC). These T cells can be subdivided into separate functional categories including cytotoxic effector cells ($T_c$), inducer or helper cells ($T_h$) and suppressor cells ($T_s$).

T cells mature in the thymus, in contrast to B cells which differentiate in the fetal liver or bone marrow. Among the cell surface molecules which characterize T cells are the $\alpha$ and $\beta$ chains of the T-cell receptor molecule. General introductory review articles describing the T-cell receptor include Toyonaga and Mak, (1987) "Genes of the T-Cell Antigen Receptor in Normal and Malignant T-Cells" in *Ann. Rev. of Immunology* 5:585-620; Kronenberg et al., (1986) "The Molecular Genetics of the T-Cell Antigen Receptor and T-Cell Antigen Recognition" in *Ann. Rev. of Immunology* 4:529-591; and Davis, (1985) "Molecular Genetics of the T-Cell Receptor Beta Chain" in *Ann. Rev. of Immunology* 3:537-560, each of which is incorporated herein by reference.

T-cell antigen receptor polypeptides are members of the immunoglobulin superfamily. Members of the immunoglobulin superfamily are characterized by similarities in primary and tertiary structure. They also display characteristic gene segment organization, ontogeny of expression and diversification. In particular, the polypeptide chains of the immunoglobulins typically result from the rearrangement, at the genetic level, of various variable region (V), joining region (J), and constant regions (C) gene segments, or V, diversity region (D), J and C gene segments. Although particular chains may have different sized repertoires of the various segments, the genetic rearrangements and combinatorial joining and junctional diversity all contribute in a characteristic manner to produce the extraordinary diversity of polypeptide sequences exhibited by these gene families. See, Hood et al., (1985) *Cell* 40:225-22, which is incorporated herein by reference.

A T-cell antigen receptor molecule comprises two polypeptide chains, generally an alpha chain and a beta chain, each of which exhibits two extracellular immunoglobulin-like domains. Such molecules comprise an amino terminal variable region domain (V) and a carboxy terminal constant region domain (C), more specifically designated with $\alpha$ or $\beta$ when indicating the particular chain of origin. Each of these domains is normally stabilized by a disulfide bond between two conserved cysteine residue pairs on each chain. The two chains are apparently attached to one another by an inter-chain disulfide bond near the cell membrane outer surface. Each chain is anchored on the membrane by a hydrophobic transmembrane segment which typically spans the entire membrane lipid bilayer. A short carboxy terminal segment extends into the cytoplasm. Both alpha and beta chains are normally N-glycosylated at sites near the disulfide bonds and at a site near the extracellular surface of the cell membrane.

The alpha and beta chains of the T-cell receptor are encoded by gene segments analogous to the variable region (V) segment, the joining region (J) segments, the diversity (D) segment, and the constant region (C) segments of immunoglobulin genes. Diversity in the T-cell receptor repertoire arises, in part, from the rearrangement of V, D, and J gene segments and from the insertion or deletion of nucleotides at the $V_\beta$-D and D-$J_{62}$ or $V_\alpha$-$J_\alpha$ junctions. Some cells express T-cell receptor gamma and delta chains in place of the alpha and beta chains.

Although specimens of alpha and beta chains of T-cell antigen receptors from mouse and from human have been isolated, it has been difficult to raise antibodies of desired specificity against these polypeptides. T-cell receptors are expressed at very low levels on T lymphocytes, with conventional biochemical purification generally being unfeasible. Thus, physical characterization studies have been almost non-existent. In general, the production of antibodies against native T-cell receptors has also been unproductive.

Previous workers have reported solubilization of the T-cell antigen receptor (TCR) $V_\alpha$ domain as a chimeric molecule in either the form $V_\alpha$-$C_{H1}$-H-$C_{H2}$-$C_{H3}$ or the form $V\alpha C\kappa$, where $C_{H1}$-H-$C_{H2}$-$C_{H3}$ and $C_\kappa$ are, respectively, immunoglobulin heavy and light constant regions. See Gascoigne et al., (1987) *Proc. Natl. Acad. Sci. USA* 84:2936-2940; Mariuzza and Winter, (1989) *J. Biol. Chem.* 264:7310-7316). Gascoigne et al. reported solubilizing the chimeric $V_\alpha$-heavy chain in conjunction with a mouse $\lambda$ light chain, whereas Mariuzza and Winter reported solubilizing the chimeric $V_\alpha C_\kappa$ light chain homodimers expressed in the absence of heavy chain expression.

Consistently obtaining highly efficient, secreted expression of substantially full length T-cell receptor polypeptide segments remains a major research goal. Although some genetic fusions between T-cell receptor domains and immunoglobulin segments have been constructed, the expression products typically have resulted in insoluble polypeptides. Thus, there exists a need for improved methods for producing large quantities of water-soluble T-cell receptor analogues which will permit the efficient production of antibodies against natural T-cell receptor epitopes. Preferably, when presented to target immune systems the analogues will not induce a significant number of antibodies against epitopes from the non-TCR segments. In particular, polypeptide segments of T-cell receptors which can be effectively reconstituted into conformations highly analogous to their native state would be most preferred.

Furthermore, the absence of a full repertoire of reagents for distinguishing the various T-cell receptor family types has hindered progress in the understanding and treatment of many immunological disorders. The present invention answers these and other needs.

SUMMARY OF THE INVENTION

The present invention provides for the efficient production of antibodies, typically monoclonal antibodies (MAbs), to human T-cell antigen receptor (TCR) epitopes. These antibodies have numerous uses as research, diagnostic, and therapeutic tools for studying or treating immune processes mediated by T-lymphocytes. A pre-requisite to the development of these antibodies is the availability of sufficient amounts of immunogen, in this case, proteins comprising human TCR epitopes, in highly pure form.

A preferred soluble chimeric polypeptide of the present invention will have at least 100 amino acids from a $V_\beta$ domain, typically a complete native human $V_\beta$ domain. The solubility may be conferred by an immunoglobulin heavy chain CH2 or CH3 domain fused to the $V_\beta$ domain. Alternatively a polypeptide comprising $X1-V_\beta-C_\beta-X2-CH2-CH3-X3$ can be prepared, wherein
  $V_\beta$ is a variable region domain of a human T-cell receptor $\beta$ chain (e.g., $V_\beta 8.1$);
  $C_\beta$ is a constant region domain of a human T-cell receptor $\beta$ chain;
  CH2 is a second heavy chain constant region domain of an immunoglobulin gene;
  CH3 is a third heavy chain constant region domain of an immunoglobulin gene; and each of X1, X2 and X3, if present, is a polypeptide segment comprising less than about 50 amino acids.

A preferred method for producing antibodies capable of binding to a $V_\beta$ T cell receptor domain epitope will comprise the step of exposing to a target immune system a soluble hybrid polypeptide comprising a $V_\beta$ T-cell receptor domain. Thereafter, one or more cell lines capable of producing the antibodies can be cloned. Alternatively, the antibodies can be produced by exposing to a target $V_\beta$ hybrid polypeptide on a cell surface. The antibodies are useful in various therapeutic regimens and diagnostic systems.

BRIEF DESCRIPTION OF THE FIGURES

FIG. 3 depicts the deletion of transmembrane domains from $\beta$-TCR.

FIG. 5 represents the amino acid sequence from the amino-terminus of the chimeric V$\beta$8.1/mouse $\gamma$2a protein.

DETAILED DESCRIPTION

Figure 1A:
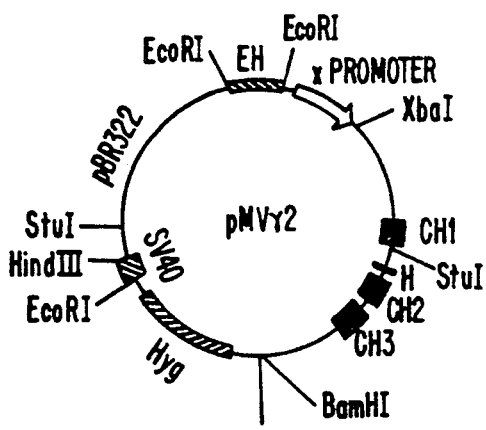
FIG. 1A is a map of pMV$\gamma$2. $E_H$ is the Ig heavy chain enhancer; $C_{H1}$, H, $C_{H2}$, and $C_{H3}$ represent, respectively, the mouse $\gamma$2a heavy chain constant region 1, hinge, constant region 2, and constant region 3 domains. Hyg represents the hygromycin resistance gene.

The present invention provides novel nucleic acid constructs which, upon expression, produce polypeptides useful for immunizing target immune systems to raise antibodies specifically reactive with native T-cell receptor epitopes. The antibodies exhibit specific binding to native conformation epitopes to provide powerful diagnostic and therapeutic reagents. The present invention also provides generalized techniques for producing fusion polypeptides which are, typically, both soluble and secreted, and possess structural features exhibiting unusually high epitopic similarity to native T-cell receptor molecular structures.

In accordance with one aspect of the present invention, novel gene fusions are provided which comprise a T-cell receptor extracellular domain, such as the variable and constant domains of a T-cell receptor polypeptide chain, and constant region domains of another immunoglobulin superfamily gene, typically a mouse IgG heavy chain lacking a complete CH1 domain. The resulting gene fusion encodes a hybrid polypeptide than can be secreted by the producing cell in a soluble form, preferably with post-translational modifications characteristic of polypeptides naturally occurring in T cells. By careful selection of a combination of a desired T-cell receptor $V_\beta$ gene and immunoglobulin gene domains, as guided by the rules described herein, the natural conformations of the T-cell receptor domains and the immunoglobulin domains are substantially obtained.

A preferred embodiment of the present invention includes the use of these improved antigens to efficiently produce polyclonal or monoclonal antibodies specific for a selected T-cell receptor molecular structure, in some instances substantially free of any immunological response to the non-TCR epitopes or to unnatural conformational epitopes. The present invention also includes the antigens themselves, their use in structural and functional characterizations, and the uses of both antigens and their reactive antibodies as diagnostic, therapeutic or investigative agents.

General Definitions

In order that the invention may be more completely understood, several definitions are set forth. As used herein, the term "immunoglobulin" refers to a protein substantially encoded by one or more immunoglobulin gene segments. The recognized immunoglobulin genes include $\kappa$, $\lambda$, $\alpha$, $\gamma$, $\delta$, $\epsilon$, and $\mu$ constant region genes, as well as the myriad immunoglobulin variable region genes. See, generally, Hood et al., *Immunology*, 2nd Ed. (1984) Benjamin Pub. Co., Menlo Park, Calif., which is incorporated herein by reference.

The T-cell antigen receptor (TCR) appears to comprise at least two different polypeptide chains in a heterodimer complex. This complex normally contains one alpha polypeptide chain and one beta polypeptide chain. These two chains are normally held together by an inter-chain disulfide bond. Each of the alpha and beta chains contains one segment designated a variable region (V), and one segment designated a constant region (C). Analogous to the alpha chain, the variable and constant regions of the beta chain are designated $V_\beta$ and $C_\beta$, respectively. In addition to the variable and constant regions, each chain possesses a relatively hydrophobic transmembrane segment and a short intracellular domain.

T-cell antigen receptor V genes may also be categorized into categories, either families or subfamilies. Each subfamily can be characterized by a consensus sequence and contains similar gene segments exhibiting greater than about 75% similarity in the DNA sequence. Sixteen mouse $V_\beta$ sequences have been categorized into fourteen different subfamilies by a proposed arbitrary but simple numerical nomenclature for the $V_\beta$ gene segments. See Barth et al., (1985) "The Murine T-cell Receptor Employs a Limited Repertoire of Expressed $V_\beta$ Gene Segments" Nature 316:517-523, which is incorporated herein by reference. According to this nomenclature, members of the same subfamily share the first digit and differ in second; therefore the $V_{\beta 8.1}$, $V_{\beta 8.2}$ and $V_{\beta 8.3}$ are all members of the $V_{\beta 8}$ subfamily. A similar system has been proposed for the human gene segments, and at least subfamilies $V_\beta 1$-$V_\beta 20$ have been identified (see, Toyonaga and Mak, op. cit., at pg. 602).

A "soluble" antigen or polypeptide is characterized by its failure to be sedimented at room temperature under low G-force centrifugation out of an aqueous buffer. Typically, a protein is considered soluble if the protein, at a temperature greater than about 5° C., at near neutral pH in the presence of low or no concentrations of detergent, has a sedimentation value less than about 10 to 50 svedberg units. Solubility is particularly important in providing simplicity in purification of the hybrid T-cell antigen polypeptide from the producing cell and in presentation of the purified antigen to an immune system to elicit highly specific antibodies. Solubility is also important for use of the fusion polypeptide as a binding receptor for either ligand specific reagents or cognate antigens. Secretion of the hybrid immunogen is also important to maximize ease of purification from producing cells. Aqueous buffers used in protein chemistry typically have a buffering compound for providing a pH, typically within a physiological range of about 5-9, an ionic strength typically between about 10 mM and about 500 mM, often a protease inhibitor and a mild detergent. Often a carrier protein may be added, such as bovine serum albumin (BSA) or chicken ovalbumin to a few mg/ml. Examples of standard buffers are phosphate buffered saline, tris-buffered saline or any of a number of buffers used in protein isolation. *See generally*, volumes of Methods in Enzymology; Mahler and Cordes (1966) *Biological Chemistry* (2d Ed.) Harper and Row, New York.

A "natural conformation" for a polypeptide domain is that secondary and tertiary conformation of the domain in a hybrid protein exhibiting substantially identical epitopes to a target immune system as the native polypeptide would by itself. Such includes, preferably, immunoantigenic determinants co-translationally or post-translationally supplied, as by glycosylation or modification of amino acid residues or other structural components. Optimally, the tertiary structure of the hybrid polypeptide closely approximates that of a native homologous segment in its natural state, typically in a natural membrane integrated form. In particular, the spatial relationship and tertiary and macromolecular structure of the hybrid domains should retain virtually identical intrachain relationships such that the immunological epitopes eliciting antibodies in a target immune system are substantially identical to the structural features of a natural homologous structure. See Watson et al. (1987) *Molecular Biology of the Gene*, Benjamin Pub. Co., Menlo Park, Calif., hereby incorporated herein by reference.

The term "operably linked" means that a genetic sequence is operationally linked to nucleic acid segments or sequences either upstream or downstream from a given segment. Those nearby segments typically affect processing or expression of the given nucleic acid sequence.

A target immune system is comprised of essential T cells and B cells as necessary to biologically effect the desired immunological response. Such immune systems will typically be intact animals. Antigens are presented to such animals by injection, with or without appropriate adjuvants. Such immunization should thereby present molecular epitopes to the immune system in a fashion that allows the T cells and B cells to interact to produce the desired response. Alternatively, such presentation may be performed in vitro under specifically controlled conditions. See, C. Reading, *J. of Immunol. Methods* (1982) 53:261-291, which is incorporated herein by reference.

In many instances, a target immune system may be substituted by a library of antibody producing cells. See. Huse et al. (1989) "Generation of a Large Combinatorial Library of the Immunoglobulin Repertoire in Phase Lambda" Science 246:1275-1281, herein incorporated herein by reference. Thus, a broad repertoire of available gene constructs may be screened to serve either as sources for producing antigens or for antibodies against specific antigens. Recombinant antigens or antibodies may be produced by gene fusion methods described, e.g., in Cabilly et al., U.S. Pat. No. 4,816,567; Boss et al., U.S. Pat. No. 4,816,397 and Winter, EPO 0239400, each hereby incorporated herein by reference. These references describe sources for the various immunoglobulin domains useful in the fusion proteins of the present invention, along with alternative molecules which may be used as antigens or antibodies.

Finally, in some situations, particularly in production of antibodies, single chain molecules may be substituted, as described in, e.g., Huston et al., *Proc. Natl. Acad. Sci. USA* 85:423-26 (1988); Bird et al., *Science* 323:15-16, each hereby incorporated herein by reference.

An "accessible" cell surface protein is one that, as associated with a cellular structure, is immunogenic when presented to an appropriate target immune system. Thus, a polypeptide whose epitopes are structurally protected from a target immune system is not considered immunologically "accessible".

An "immunotoxin" is a molecule which comprises both a targeting moiety and a toxic moiety. Typically, the targeting moiety is an antibody binding site. The toxic moiety is toxic to the cell or structure to which the targeting moiety attaches. Thus, one form of an immunotoxin is an antibody conjugated to a toxic compound or reagent, such as ricin, providing a functional highly specific targeting of the toxin. Immunotoxins are reviewed in I. Pastan et al., *Cell* 47:641–648 (1986). Recently, recombinant immunotoxins have been developed (Chaudhary et al., *Nature* 339:394–399).

Design Considerations

In accordance with the present invention, genetic constructs have been devised to express polypeptide immunogens mimicking T-cell receptor epitopes. These chimeric polypeptides will preferably be readily secreted in soluble form at high expression levels by cells transformed with the genetic constructs.

An exemplary genetic construct comprises a chimeric human T-cell receptor (TCR)/IgG construct domain compound, preferably without a CH1 domain. A chimeric protein results from the fusion of polypeptide segments originating from different proteins. The resultant protein, also known as a fusion protein, typically exhibits some biological or physical properties of each of the proteins from which the chimera is derived. Thus, fusion proteins of a signal sequence with another protein may result in secretion of an otherwise cytoplasmic protein. Such techniques may provide for proteins exhibiting properties in a single protein characteristic of each individual parent, often from different species. Examples of chimeric proteins include chimeric antibodies providing for molecules exhibiting mouse binding domains and human constant region domains, and fusion between $\beta$-galactosidase and other proteins (for determining insertion of cloned segments).

Since hybridoma technology is best understood in the mouse, the preferred embodiment utilizes a human $V_\beta C_\beta$ gene fused with a mouse immunoglobulin gene fragment. This fusion provides that the human TCR portion of the chimeric polypeptide serves as the focus of the immune response when exposed to a target mouse immune system. It will be understood that other target immune systems and a corresponding immunoglobulin gene may be substituted for mouse as detailed below.

Because there are inter-chain contact regions between the variable domain and the constant domain of the beta chain of the T-cell receptor, the antigens of a preferred embodiment of the present invention present a more natural conformation between the variable and constant domains of the beta receptor by containing both of these domains as found in a natural beta chain. Molecular modeling studies have been performed on immunoglobulin molecules based upon X-ray crystallographic studies. These studies have indicated the presence of a ball and socket type of contact between amino acid residues in $V_H$ and $C_{H1}$ of the antibody heavy chain. See. Lesk and Chothia, (1988) *Nature* 335:188–190, which is incorporated herein by reference. These contact residues have been hypothesized as being important for a conformational change occurring upon antigen binding by the antibody molecule. A homology search for similar residues at equivalent positions in T-cell receptor sequences revealed the presence of such residues in the $\beta$-TCR sequence, but not in the $\alpha$-TCR sequence. Hence in the context of these studies, prior investigators were forcing a very unnatural juxtaposition of dissimilar residues between $V_\alpha$ and $C_{H1}$ by substituting $V_\alpha$ for $V_H$.

Finally, in the preferred constructs of the present invention, there is no need to produce multiple chains of T-cell receptors, thus eliminating the requirement for coordinated processing between different chains. By appropriate selection of cells for expression, the glycosylation patterns of the beta chain may be slightly modified. Moreover, it is possible to co-transform a similar construct with the alpha chain of the T-cell receptor with another construct containing the beta chain of the T-cell receptor, thereby providing the possibility for association into homodimers of alpha and of beta and heterodimers of alpha with beta.

An exemplary chimeric polypeptide of the present invention is a chimeric human T-cell receptor beta chain/mouse IgG$\beta$2a heavy chain protein. The preferred genetic construct contains the human $\beta$ chain 8.1 subtype (YT35), but any other $\beta$ T-cell type may be substituted. The construct is designed to contain: L$\beta$-V$\beta$-D$\beta$-J$\beta$-C$\beta$(delta TM)-H-C$_H$2-C$_H$3, where L$\beta$-V$\beta$D$\beta$-J$\beta$ denote one leader peptide, V region, D region and J region of a beta T-cell receptor chain; C$\beta$(delta TM) denotes the constant region of a beta T-cell receptor gene with the transmembrane and intracellular segments deleted (i.e., the 48 carboxy terminal amino acids of the polypeptide); and H—C$_H$2—C$_H$3 denote a mouse IgG$\gamma$2a heavy chain hinge, second constant region and third constant regions.

Alternative chimeric constructs of the present invention include combinations of the various $V_\beta$, $C_\beta$, $V_\alpha$, $C_\alpha$ with constant region domains from immunoglobulins. Thus, alternative constructions include use of less than full length segments of the TCR domains. Thus instead of using full length $V_\beta$ or $C_\beta$ domains in the described constructs, smaller segments of the domains may be substituted. These segments will ordinarily be at least about 50 amino acids from the appropriate domains, such as the $V_\beta$ or $C_\beta$ domains, preferably at least about 80 amino acids and, in preferred embodiments, up to the full length of the domain.

Alternatively, segments from proteins other than immunoglobulins might be used, and may include proteins from other species. Typically, the non-TCR domains are included for the purpose of conferring either secretion or solubility properties to the chimeric protein. Other useful segments such as ovalbumin, serum albumin, and other soluble proteins might be selected. But typically, immunoglobulin gene family domains will be used, more usually constant domains from immunoglobulin genes, from the mouse or other species. Thus, constant region domains from other species may be substituted.

The fusion proteins also may include between each of the specified domains, either additional domains or spacer segments of polypeptide. Such domains will typically be globular domains which will not interfere with the TCR domains. Spacer segments will typically be selected under similar constrains, but will typically be less than about 200 amino acids, preferably less than about 50 amino acids; more preferably less than about 30 amino acids, and in the preferred embodiment, fewer than 10 amino acids.

As the domains, as described, may be less than the entire domain, the hinge region of the CH2 domain proximate to the TCR domains may be deleted as well. Likewise, the $C_\alpha$ or $C_\beta$ domains may be less than the entire domain. In the extreme, particular domains may be totally deleted, for example, one of the constant regions domains may be removed.

Additions to the described domains may be included. For example, either immunoglobulin or non-immunoglobulin transmembrane or cytoplasmic domains may be added providing for expression of the antigen on a cell surface. Typical transmembrane domains include those from the TCR proteins or other cell membrane proteins, from the same or other species.

Besides the expression of single chain proteins, the present invention includes multichain antigens. Among the multichain embodiments are combinations of α chain type fusion proteins with β chain type fusion proteins. For example, simultaneous expression, perhaps coordinate, of $V_\alpha C_\alpha C_{H2} C_{H3}$ with $V_\beta C_\beta C_{H2} C_{H3}$ type chains may result in heterodimer formation leading to interchain $V_\alpha C_\alpha$ domains with $V_\beta C_\beta$ domains. Alternatively, an IgG type molecule may result from coexpression of $V_\alpha C_\alpha$ type protein with the fusion protein of $V_\beta C_\beta$ immunoglobulin domains, or the $V_\beta C_\beta$ type protein with a fusion protein of $V_\alpha C_\alpha$-immunoglobulin domains.

The DNA segments will typically further include an expression control DNA sequence operably linked to the chimeric polypeptide coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the polypeptides containing the $V_\beta$ epitopes.

Human $V_\beta$ domain DNA sequences can be isolated in accordance with well known procedures from a variety of human cells, but preferably peripheral T-cells. The immunoglobulins and other domains for producing the chimeric proteins of the present invention will be similarly derived from B cells. They may be obtained from any convenient mammalian source, including, mice, rats, rabbits, or other veterbrate capable of producing antibodies by well known methods. Suitable source cells for the DNA sequences and host cells for immunoglobulin and other protein expression and secretion can be obtained from a number of sources, such as the American Type Culture Collection ("Catalogue of Cell Lines and Hybridomas," Fifth edition (1985) Rockville, Md., U.S.A. which is incorporated herein by reference). Immunoglobulin domains have been well defined and particular sequences may be found in, e.g., E. Kabat et al., "Sequences of Proteins of Immunological Interest" U.S. Dept. Health and Human Services (1983), hereby incorporated herein by reference.

In addition to the chimeric polypeptides specifically described herein, other "substantially homologous" modified immunoglobulins can be readily designed and manufactured utilizing various recombinant DNA techniques well known to those skilled in the art. For example, the CH2 and CH3 domains can vary from the native sequences at the primary structure level by several amino acid substitutions, terminal and intermediate additions and deletions, and the like. In general, modifications of the genes may be readily accomplished by a variety of well-known techniques, such as site-directed mutagenesis (see, Gillman and Smith, *Gene* 8:81-97 (1979) and Roberts, S. et al, *Nature* 328:731-734 (1987), both of which are incorporated herein by reference).

The nucleic acid sequences of the present invention capable of ultimately expressing the desired chimeric polypeptides can be formed from a variety of different polynucleotides (genomic or cDNA, RNA, synthetic oligonucleotides, etc.) and components (e.g., J, D, and C regions), as well as by a variety of different techniques. Joining appropriate genomic sequences is presently the most common method of production, but cDNA sequences may also be utilized (see, European Patent Publication No. 0239400 which is incorporated herein by reference).

As stated previously, the DNA sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see. e.g., U.S. Pat. No. 4,704,362, which is incorporated herein by reference).

Cell Transformation with the Gene Fusions

Having constructed gene fusions, according to design considerations as described, expression of the antigen products is desired. Appropriate vectors and cell types may be selected which will produce an antigen or reagent which most closely parallels the desired product. For immunogen purposes, it is expected that glycosylation may be one of the primary criteria upon which a cell type selection will be based. Thus, particular cell types may be chosen for their expression properties. In other circumstances, efficiency in secretion or some other cellular property may be more desirable.

Although microorganisms may be used, eucaryotic cells are preferred to express and produce the polypeptides of the present invention (see, Winnacker, "From Genes to Clones," VCH Publishers, N.Y., N.Y. (1987), which is incorporated herein by reference). Mammalian cells are actually most preferred, because a number of suitable host cell lines capable of secreting intact immunoglobulin-like proteins have been developed in the art, and include the CHO cell lines, various COS cell lines, HeLa cells, myeloma cell lines, etc., but preferably transformed B-cells or hybridomas. Expression vectors for these cells can include expression control sequences, such as an origin of replication, a promoter, an enhancer (Queen, C., et al., *Immunol. Rev.* 89:49–68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, adenovirus, Bovine Papilloma Virus, and the like.

The vectors containing the DNA segments of interest (e.g., the $V_\beta$ domain and CH2 domain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, generally. Maniatis, et al., *Molecular Cloning: A Laboratory Manual,* Cold Spring Harbor Press, (1982), which is incorporated herein by reference.)

Once expressed, the chimeric polypeptides of the present invention can be purified according to standard procedures of the art, including ammonium sulfate precipitation, affinity columns, column chromatography, gel electrophoresis and the like (see. generally, Scopes, R., *Protein Purification,* Springer-Verlag, N.Y. (1982)).

Substantially pure polypeptides of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See. generally, *Immunological Methods*. Vols. I and II, Lefkovits and Pernis, eds., Academic Press, New York, N.Y. (1979 and 1981), which is incorporated herein by reference).

Antibodies

Once the antigens of the present invention have been constructed and expressed, thereby producing soluble and/or secreted proteins for use as antigens, antibodies may be produced by presenting the hybrid protein to a target immune system. For production of polyclonal antibodies, an appropriate target immune system is selected. Typically a mouse is used, of the appropriate strain, usually producing heavy chains of the type selected for the fusion domains of the hybrid antigen. The substantially purified antigen is presented to the immune system in a fashion determined by the mouse strain and other parameters well known to immunologists. Typical sites for injection are in the footpads, intramuscularly, intraperitoneally, or intradermally. Of course, different animals may be substituted for a mouse.

Typically, an immunological response is assayed by use of an immunoassay. Normally such immunoassays involve some purification of a source of antigen, for example, produced by the same cells and in the same fashion as the antigen was produced. The immunoassay may be a radioimmunoassay, an enzyme-linked assay, a fluorescent assay, or any of many other choices, most of which are functionally equivalent but may exhibit advantages under specific conditions.

Monoclonal antibodies with affinities of $10^8$ $M^{-1}$ preferably $10^9$ to $10^{10}$, or stronger will typically be made by standard procedures as described, e.g., in Harlow and Lane (1988), *Antibodies: A Laboratory Manual*, Cold Spring Harbor Laboratory or Goding (1986), *Monoclonal Antibodies: Principles and Practice* (2d edition) Academic Press, New York, which are hereby incorporated herein by reference. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen. Note that because the heavy chain regions of the hybrid antigen can be selected to be non-immunogenic in the target immune systems, there is inherently an advantage in the screening of the resultant monoclonal antibody supernatants since clones producing antibodies specific for the immunoglobulin heavy chains should be rare.

It will be appreciated by those of skill in the art that the binding regions of the antibody molecules contain critical amino acid residues for contact and binding in epitope recognition. Thus, these complementarity determining regions (CDR's) which produce specificity of binding are the structural features conferring specificity in binding. For the binding functions of these antibodies, molecules which exhibit sufficiently similar spatial relationship of these CDR's will be functionally equivalent molecules. Gene fusions or deletions leading to molecules which provide CDR's based on antibodies of the present invention will obviously serve, in many cases, to provide equivalent functions.

Selecting Specific $V_\beta$ Antibodies

One important objective of this invention is the development of an array of antibodies capable of distinguishing the various forms of the T-cell receptor molecules. Thus, it is desirable to produce antibodies analogous to anti-idiotypic antibodies of immunoglobulin genes.

A large array of antigens might be produced from different $V_\beta$ chains against which each of a large number of different T-cell receptor specific antibodies might be tested. By comparing which antibodies are specific for a single or few subfamilies or specific $V_\beta$ chains, those antibodies will become diagnostic for particular receptor subfamilies or chains. Antibodies which show broad specificity for most or all subfamilies find different uses in diagnostic or therapeutic contexts as described below.

Diagnostic, Therapeutic and Investigative Utilities

The present invention provides means for the efficient and economical production of antibodies directed to each of the various T-cell receptor chains, most typically the beta chain. By providing the means for producing enormous amounts of a soluble and secreted antigen which elicits, specifically, only antibodies reactive with the desired structural domains, the immunization of target immune systems is dramatically simplified. This allows the generation of a large repertoire of antibodies specific for binding to individual members of T-cell types, families, subfamilies or combinations.

The hybrid polypeptides of the invention are also useful in structural and functional studies on the T-cell receptor. Besides serving as substrates or binding domains of specific forms of receptor, these analogues may serve as subjects for conformational studies which approximate the native configurations. Such studies provide approximate structural or functional data which might be easily verified with smaller amounts of native TCR chains.

The solubilized chimeric receptors also serve as binding competitors to block normal cellular binding of particular ligands, thus serving to clear the ligand or to compete with the physiological binding by cells. Thus, these antigens which exhibit binding domains with the native protein binding specificity may be used in a fashion equivalent to standard antibodies for certain purposes.

These antigens may also be used to simulate the native binding domain to investigate what ligand may serve as an agonist or antagonist for the selected fusion polypeptide. Thus, the binding domain is used as a screen to select those ligands which will bind to the encoded beta chain variable region.

With the antibodies of the present invention, a repertoire of antibodies may be generated which can easily distinguish the particular type, family or subfamily of a given cell. Thus, if a clonally overproduced cell type is produced, as may occur in, for example, a leukemia condition, it is possible to determine the type of cell involved, and then a targeted immunotoxin is readily produced for eliminating those cells. Determination of the cell type can also serve as a diagnostic tool for the purpose of investigation into the problems of, or the treatment of a condition. The use of antibodies raised against T-cell receptors have been successful in treating experimental allergic encephalomyelitis (EAE). See, e.g., Acha-Orbea et al. (1988) Cell 54:263-273; and Urban et al. (1988) Cell 54:577-592.

In addition, the antibodies or binding proteins of the present invention are useful as idiotypic antibodies to determine specifically what T-cell receptor or antigen molecules are expressed within an organism. Such may be important in, among other disorders or diseases, T-cell malignancies, autoimmune diseases, transplant/graft rejection reactions, host versus graft disease, cancers, solid tumors, allergies and various infectious diseases. Quantitative or qualitative measurement of types of expressed T-cell antigen receptors will allow diagnosis and monitoring of a patient with multiple infections or a disease involving a plurality of responses.

Accordingly, patient samples are tested for expression of characteristic T-cell receptors. Test samples may comprise biological fluids including but not limited to blood, plasma, serum, saliva, urine, spinal fluid, synovial fluid, amniotic fluid and cranial fluid. Quantitation may be performed by comparison to known standard samples.

The following examples are offered by way of illustration, not by limitation.

EXPERIMENTAL

Vector

1. Deletion of CH1 exon from the expression vector.

Figure 1B:
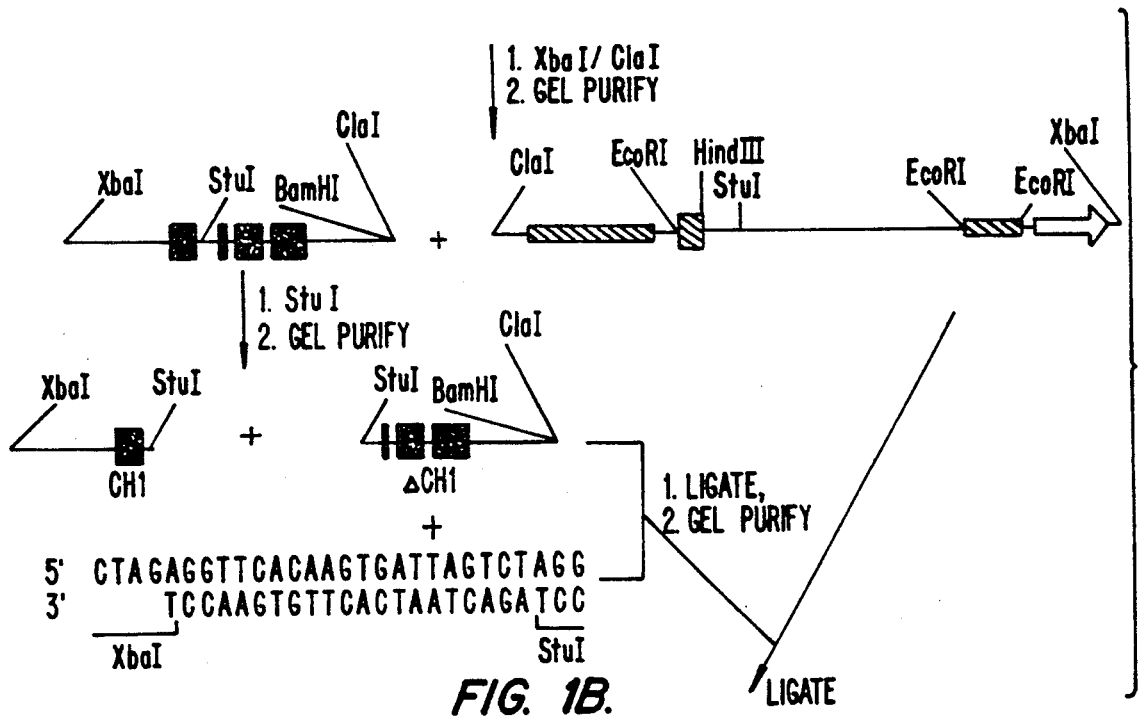
FIG. 1B is a schematic description of steps involved in deleting the CH1 exon. The $\Delta C_{H1}$ fragment was first ligated with the adapter oligonucleotide shown, further gel purified, and then used in the final ligation step with the vector fragment to generate the construct shown in FIG. 1c, which is a map of pMV$\gamma$2($\Delta C_{H1}$).

The antibody domains chosen for incorporation into the chimeric $\beta$-TCR construct were derived from the vector pMV$\gamma$2. This vector was itself derived by replacing the XbaI-BamHI fragment of PV$\gamma$1 (Queen et al. (1989), *Proc. Natl. Acad. Sci. USA* 86:10029-10033) containing the human constant region with an XbaI-BglII fragment containing the mouse $\gamma$2a constant region, a ClaI linker being used to connect the BamHI and BglII ends. A map of pMV$\gamma$2 along with pertinent structural features and relevant restriction sites is presented in FIG. 1A. The vector contains the full mouse gamma 2a constant region downstream of a unique Xba I cloning site. The first modification of the vector involved deletion of the $C_{H1}$ exon. This was accomplished as outlined in FIG. 1B. Specifically, 50 $\mu$g of pMV$\gamma$2 were digested with Xba I and Cla I to produce a 6.7 kb "vector" fragment, and a 4.1 kb fragment containing the full mouse gamma 2a constant region. These fragments were recovered by electroelution following fractionation on a preparative 0.9% Agarose gel. In order to delete the $C_{H1}$ exon from the $\gamma$2a fragment, the 4.1 kb Xba I/Cla I fragment was subsequently digested with Stu I. Stu I cuts in the intron between the $C_{H1}$ and Hinge (H) exons, 47 nucleotides downstream of the intron donor site. Thus, the purified 4.1 kb $\gamma$2a fragment was further digested with Stu I, and the resultant 1.6 kb Xba I/Stu I "$C_{H1}$ fragment" and 2.3 kb Stu I/Cla I fragments recovered following a second round of agarose gel fractionation and electroelution. The 2.3 kb Stu I/Cla I fragment, which contains the Hinge (H), and second and third heavy chain constant region exons ($C_{H2}$, $C_{H3}$), will be henceforth referred to as the $\Delta C_{H1}$ fragment. The $\Delta C_{H1}$ fragment was ligated with the following synthetic adapter oligonucleotide to restore an Xba I site at its 5' end:

5' <u>C</u>TAGAGGTTCACAAGTGATTAGTCTAAGG 3'
3'     TCCAAGTGTTCACTAATCAGATTCC 5' the sequence of this adapter oligonucleotide is derived from the naturally occurring sequence in the intron between the $C_{H1}$ and H exons for 28 of the 29 nucleotides upstream of the Stu I site in this intron. The first nucleotide of this oligo, shown underlined, was modified from the naturally occurring nucleotides so as to reconstitute the desired Xba I site. The naturally occurring nucleotide at this position in the intron is a G. The first three nucleotides of the hexanucleotide Stu I site are highlighted in boldface.

Figure 1C:
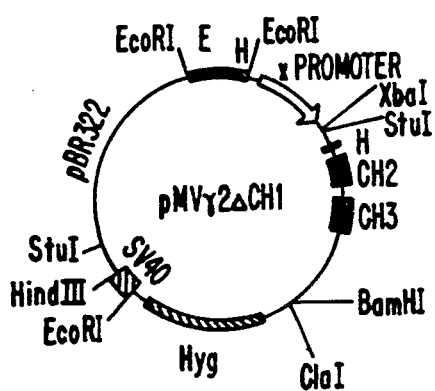
FIG. 1 depicts the deletion of CH1 exon from pMV$\gamma$2.

The adapter ligated 2.3 kb $\Delta C_{H1}$ fragment was purified away from unligated excess adapter by fractionation on an agarose gel and recovered by electroelution. Finally, this was religated to the 6.7 kb Xba I/Cla I "vector" fragment from step 1 above to reconstitute a $\Delta C_{H1}$ version of the original vector, referred to as pMV$\gamma$2($\Delta C_{H1}$), shown in FIG. 1C. Preparative amounts of this first modification of the vector were obtained by transformation of E. coli DH1 competent cells with the products of ligation of the 6.7 kb "vector" fragment and the 2.3 kb adapter ligated $\Delta$CH1 fragment. Transformed colonies were positively identified by their Amp$^r$ phenotype, and the $\Delta C_{H1}$ modified vector was purified in preparative quantities using conventional plasmid purification procedures (Sambrook et al., (1989) in *Molecular Cloning: A Laboratory Manual* (Second Edition), Cold Spring Harbor Laboratory). The sequence of the artificial junction between the Xba I and Stu I sites was verified by DNA sequence analysis of the plasmid.

2. Replacement of Immunoglobulin heavy chain promoter/kappa enhancer with the human cytomegalovirus enhancer/promoter.

Comparative studies carried out at Protein Design Labs on relative strengths of promoter enhancer combinations leading to highest levels of expression of a desired gene product have established the human cytomegalovirus (HCMV) enhancer/promoter as superior to the immunoglobulin heavy chain enhancer/$\kappa$ promoter combination for the production of humanized antibodies in myeloma cells. Since we wished to achieve the highest possible levels of expression of the chimeric V$\beta$8.1/mouse $\gamma$2a protein, we further engineered the pMV$\gamma$2($\Delta C_{H1}$) vector by replacing the immunoglobulin heavy chain enhancer/$\kappa$ promoter with the HCMV enhancer/promoter.

The HCMV enhancer/promoter was isolated as an approximately 600 bp Fnu D2 fragment extending from position $-522$ to position 72 (numbered according to Boshart et al. (1985) Cell 41:521-530), and an Eco R1 linker was added at the 5' end and an Xba 1 linker at the 3' end.

The deletion of the immunoglobulin enhancer/promoter from pMV$\gamma$2($\Delta C_{H1}$) was effected by digestion of 8 $\mu$g of pMV$\gamma$2($\Delta C_{H1}$) with Xba I and Hind III. This digest generated a 4.5 kb fragment containing the $\gamma$2($\Delta C_{H1}$) and Hygromycin$^r$ genes (referred to as fragment A) and a 4.4 kb fragment containing the Ig promoter/k enhancer, pBR322 ori sequences, and a SV40 polyadenylation fragment (referred to as fragment B). Following size fractionation by agarose gel electrophoresis and recovery by electroelution, fragment A was set aside for later use, and fragment B was subjected to secondary digestion with Eco RI. This produced 3 fragments: a 2.64 kb Eco RI/Hind III fragment containing pBR322 ori sequences, and the SV40 fragment polyadenylation signal; a 1.13 kb Eco RI/Xba I fragment containing the Ig heavy chain promoter; and a 0.7 kb Eco RI fragment encoding the κ enhancer. The 2.64 kb Eco RI/Hind III fragment was recovered by electroelution following agarose gel fractionation, and treated with alkaline phosphatase from calf-intestine to prevent self ligation and polymerization in subsequent steps.

Figure 2:
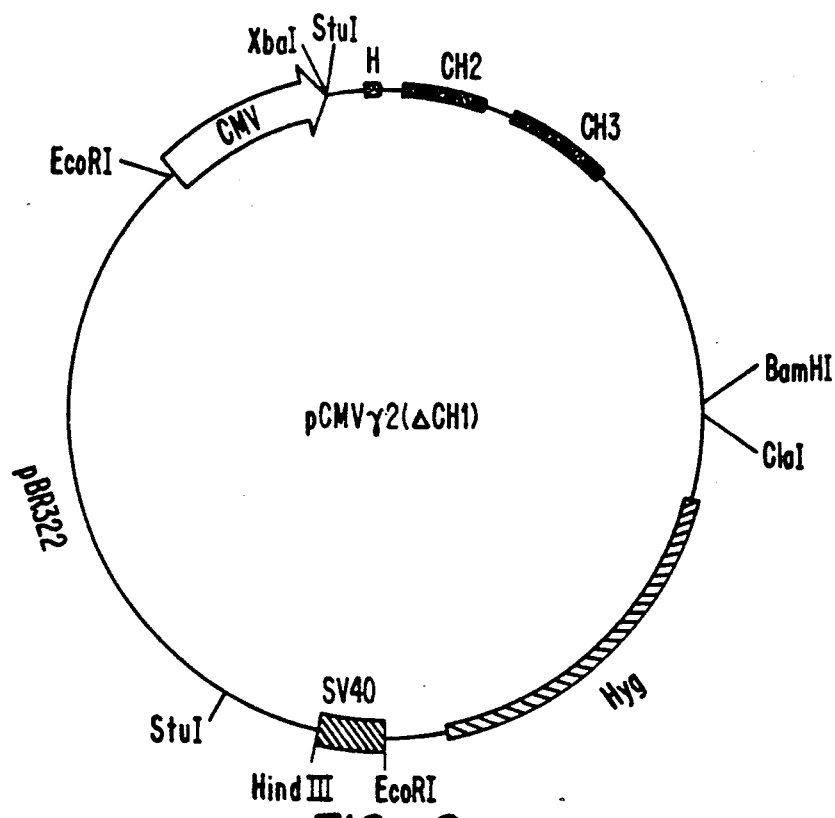
FIG. 2 is a map of pCMV$\gamma$2($\Delta C_{H1}$). CMV denotes the ~700 base pair enhancer promoter from human cytomegalovirus.

The 4.5 kb Xba I/Hind III fragment (fragment A), 2.6 kb phosphatased Eco RI/Hind III pBR322 ori, SV40 fragment, and 600 bp Eco RI/Xba I HCMV enhancer/promoter encoding fragments were combined in a triple ligation experiment to produce the desired vector, designated pCMVγ2($\Delta C_{H1}$), shown in FIG. 2. This vector was recovered by transformation of competent E. coli with an aliquot of the triple ligation reaction mixture. Potential colonies containing the desired vector construct were selected on the basis of their Amp$^r$ phenotype, and plasmid minipreps from Amp$^r$ colonies were purified and analyzed by diagnostic restriction endonuclease digests to identify those colonies containing the correct vector construct, as predicted from the map in FIG. 2.

3. Deletion of the Trans-membrane Domain from the β-TCR constant region.

A full length cDNA insert containing a functionally rearranged human Vβ8.1 T-cell receptor sequence was obtained from the clone YT35 (Yanagai et al., (1984) Nature 308:143–149) as an Xba I/Sph I fragment, and transferred into a Bluescript vector (Stratagene) and designated pBSβ8.1.

Figure 3A:
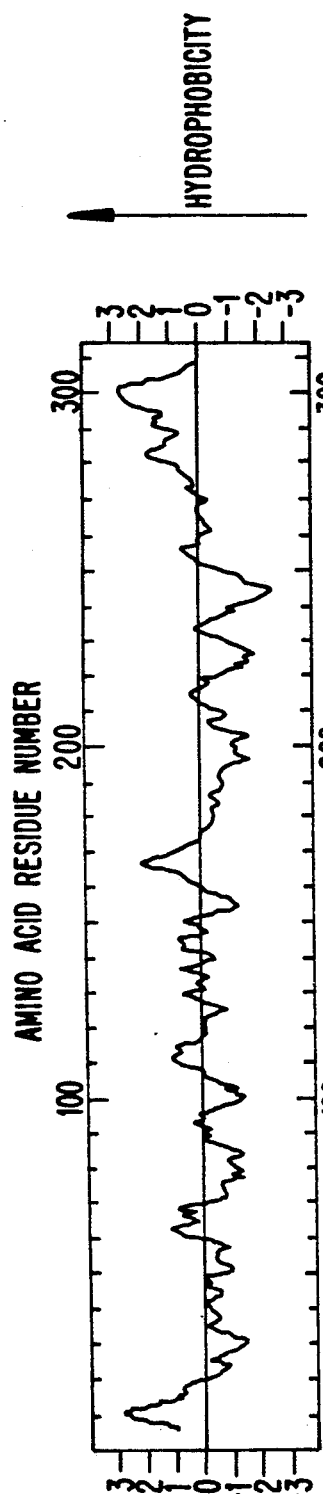
FIG. 3A is a hydropathy analysis of predicted amino acid sequence of $\beta$-TCR and its alignment with a restriction endonuclease map of the cDNA.

Hydropathy analysis (Chou and Fasman, (1978) Adv. in Enzymol. 47:45–147, hereby incorporated herein by reference) of the predicted amino acid sequence encoded by this cDNA serves to identify a putative membrane spanning region at the carboxy terminal end of this protein. A unique Stu I site is situated just upstream of the trans-membrane (TM) and cytoplasmic domains of the β T-cell receptor, and hence, serves to delineate them from the extra-cellular V,D,J,and C domains (FIG. 3A). Analytical digests of pBSβ8.1 plasmid isolated from DHI strain of E. coli, with Stu I showed the plasmid refractory to digestion with this enzyme. This was discovered to be due to a methylation modification of a cytosine residue contained within the Stu I site by dcm methylase, which rendered the site non-cleavable by Stu I (New England Biolabs, 1988–1989 product catalog, p.143). Hence, the plasmid pBSβ8.1 was transfered into E. coli HB101, which is dcm modification negative. Thus, 112 μg of pBSβ8.1, isolated from HB101 transformed cells, were digested with Xba I and Stu I. The 817 bp β-TCR insert deleted of its transmembrane domain (ΔTM) was recovered by electroelution after fractionation in 1% Agarose gel.

Figure 3B:
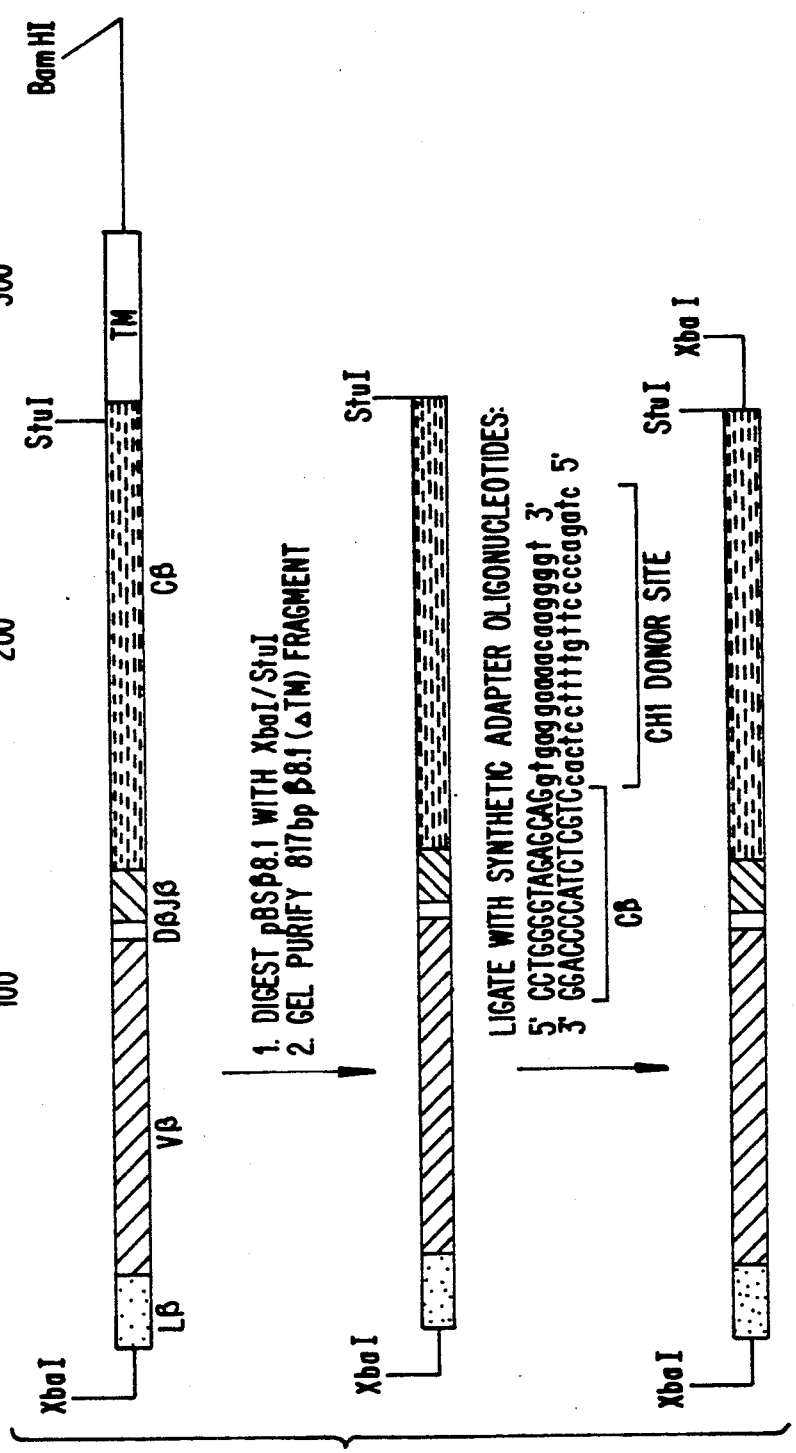
FIG. 3B shows the deletion of transmembrane domain from $\beta$-chain, and ligation with adapter oligo for subsequent cloning into Bluescript vector. Nucleotides #33 and #34 of this adapter oligonucleotide are modified from the naturally occurring nucleotides at these positions in the intron so as to introduce an Xba I site.

The purified β(ΔTM) fragment was ligated with a synthetic 37-mer oligo-nucleotide, as outlined in FIG. 3B, to restore the Stu I site abutting the fragment, and re-introduce an Xba I site at its 3' end. The first 15 nucleotides of this oligo were derived from the Cβ sequence to preserve the β-TCR residues immediately extracellular to the plasma membrane. The remaining 22 nucleotides of this oligo-nucleotide are derived from the intron donor site and the first 16 nucleotides downstream of it, in the intron between the CH1 and H exons from the vector pMVγ2. Nucleotides #33 and #34 of this adapter oligonucleotide are modified from the naturally occurring nucleotides at these positions in the intron so as to introduce an Xba I site, to facilitate cloning of the transmembrane deleted insert fragment into the (ΔCH1) modified vector (see Vector, above, and FIG. 4 below).

The adapter ligated β-TCR(ΔTM) fragment was purified from unligated adapter oligo by fractionation on an agarose gel and recovered by electroelution. It was then introduced into the Xba I site of the Bluescript vector (Stratagene) for amplification by preparative isolation of plasmid from transformed bacteria. This plasmid was designated pBSβ8.1(ΔTM).

Generation and Verification of the Final Construct

Figure 4:
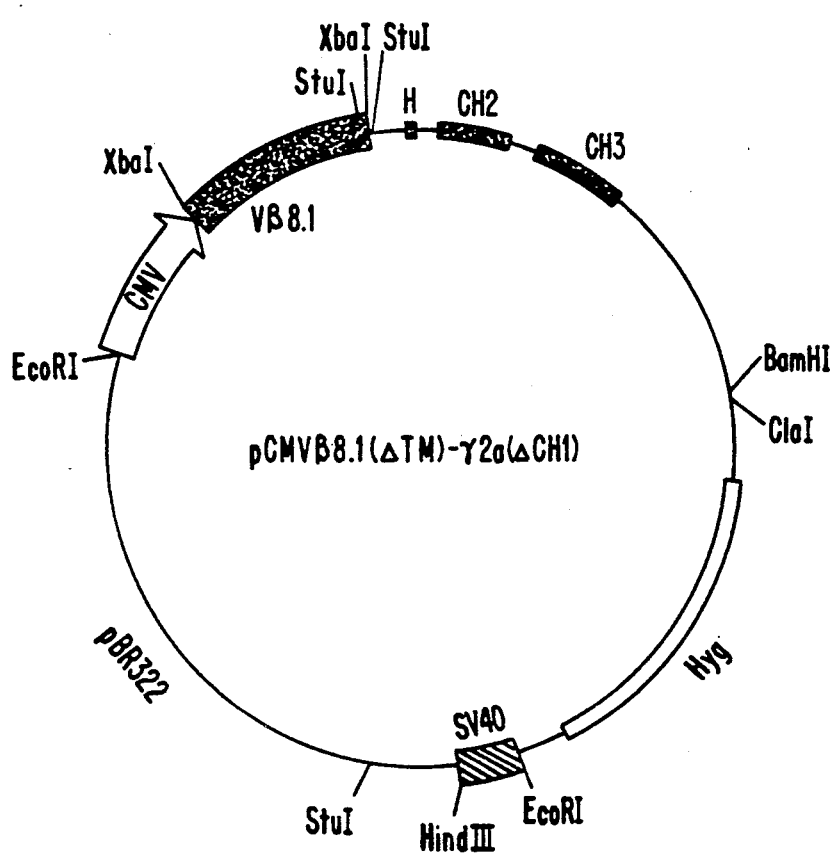
FIG. 4 is a map of the pCMV$\beta$8.12($\Delta$TM)-$\gamma$2a($\Delta$CH1) construct.

Generation of the final construct is outlined below, and a map of the construct is presented in FIG. 4. For generation of the final construct, the vector pCMVγ2($\Delta C_{H1}$) was linearized by digestion with Xba I, followed by phosphatasing of 5' termini with calf-intestinal alkaline phosphatase. Meanwhile, the ~880 bp β8.1(ΔTM) fragment was purified by electroelution of Xba I digested pBSβ8.1(ΔTM) fractionated on an agarose gel. The β8.1(ΔTM) insert was then ligated into the Xba I linearized and phosphatased vector and the products of the ligation reaction used to transform competent E. coli.

Transformed colonies were selected on the basis of resistance to ampicillin, and plasmids analyzed by diagnostic restriction digestion of "miniprep" DNAs purified from small scale cultures. The mini-prep DNAs were digested with Xba I to verify presence of an insert fragment of the expected size (880 bp). Finally, orientation of insert relative to promoter was determined by digestion of the DNAs with Stu I. Those clones with insert in the same orientation as the promoter were chosen for final sequence verification of relevant portions of the molecule. The results from DNA sequence analysis of the constructs at the 5' end of the insert and at the 3' insert/vector junction containing the artificial splice donor site, across the Xba I and Stu I sites, and into the CH1-Hinge intron, agreed exactly with the expected sequences at these junctions, and verified the correctness of the the construct. Following sequence confirmation of the identity of the constructs, the CMV enhancer/promoter construct was designated pCMVβ8.1(ΔTM)-γ2a(ΔCH1).

Expression of Chimeric T-Cell Receptor/Immunoglobulin Protein

1. Transfection of Cells and Detection of Expressing Cell Lines.

For expression of the CMV enhancer/promoter driven chimeric Vβ8.1 T-cell receptor/immunoglobulin heavy chain construct, the construct [pCMVβ8.12(ΔTM)-γ2a(ΔCH1)] was linearized with Bam HI. The linearized DNA was extracted with phenol and chloroform, ethanol precipitated, and resuspended in 1X phosphate buffered saline (PBS) at a concentration of 1 μg/μl (measured by $A_{260}$). The constructs were transfected by electroporation into two myeloma cell lines, Sp2/0, and 25-1. Sp2/0 is a B-cell tumor line which does not secrete endogenous immunoglobulins, while 25-1 is an Sp2/0 derived cell line generated at PDL, which secretes high levels of a humanized anti-TAC κ-light chain as Bence-Jones homodimers (Queen et al., (1989) Proc. Natl. Acad. Sci. USA 86:10029–10033).

Hence, $10^7$ cells in 1 ml PBS from each of these lines were transfected by electroporation (Chu et al., (1987) *Nucl. Acids Res.* 15:1311–1326) with 20 μg of the Bam HI linearized construct from above using a Bio-Rad Gene Pulser, and transformed cells were selected on the basis of resistance to hygromycin. Hygromycin selection was carried out on a daily basis, starting 24 h after transfection, by feeding the cells with media supplemented fresh daily with 700 μg/ml (±10%) hygromycin. This daily feeding was continued for 10–12 days, after which surviving cells were allowed to reach confluence in the 96-well micro-titre plating dishes. Cells were expanded in selective media by passage from the 96-well plates into 24-well plates, and supernatant aliquots were assayed for presence of chimeric β-TCR/γ2a protein by ELISA assay once the culture reached confluency in 24-well plates.

The ELISA assay for detection of the chimeric β-TCR protein was carried out as follows: ELISA plates (Immulon) were coated with 200 X dilution of goat anti-mouse IgG (Heavy+Light chain, Tago Immunochemicals) in 1X PBS at 4° C. for overnight to several days. Following blocking of non-specific protein binding sites in the plate with 1% Bovine Serum Albumin (BSA), 0.1% Tween-20, 0.01% Sodium azide in e1X PBS, for at-least 2 hours at 4° C., the plates were incubated with test antigens (supernatants from confluent 24-well plate cultures of hygromycin resistant transfected cell lines), in duplicate. The plates were incubated with antigen for 2 hours at room temperature, and then washed 3X with 200 μl/well of 1X PBS/0.1% TWEEN-20. The plates were then incubated for 1 h at room temperature with 200X dilution of horseradish peroxidase (HRP) conjugated rabbit antimouse Igγ2a (Zymed Immunochemicals) in e1XPBS as the detection reagent. Positive cell lines were identified by virtue of a green color reaction upon addition of HRP substrate (Biorad).

Table 1 below summarizes the number of expressing primary cell lines obtained from transfection of Sp2/0 and 25-1 cells with the construct pCMVβ8.1(ΔTM)-γ2a(ΔCH1).

TABLE 1

| Ratio of expressing cell lines transfected with Construct | |
|---|---|
| Cell Line | pCMVβ8.12(ΔTM)γ2a(ΔC$_{H1}$) |
| Sp2/0 | 4/10 |
| 25-1 | 32/32 |

The results show that the frequency of expression of the chimeric protein was significantly higher in 25-1 cells (>95%) than in naive Sp2/0 cells (~35%).

This difference in frequency of expression between 25-1 and Sp2/0 cells was paralleled by the level of expression of the chimeric β-chain (as measured by ELISA assay using mouse anti-TAC as a concentration standard). The highest level of expression observed from the Sp2/0 primary transfectants was 90 ng/ml for the CMV enhancer/promoter driven construct. By contrast, the highest level of expression observed in 25-1 primary transfectants was 200 ng/ml for the CMV enhancer promoter driven construct. Thus, comparing cell lines, 25-1 was superior to Sp2/0 in both the frequency of expression as well as the overall level of expression.

In summary, the data presented above from ELISA assays of supernatants from primary transfectants establish the following 3 facts: 1-The frequency of expression from transfection of the chimeric β-TCR construct is greater in 25-1 cells than in Sp2/0 cells; 2-The overall level of expression attained is greater from 25-1 cells than from Sp2/0 cells; and 3-The transfectants observed are secreting a protein which contains mouse immunoglobulin-γ2a determinants.

2. Immunochemical Characterization of The Secreted Protein.

The ELISA data presented above established, at a preliminary level, the secreted expression of a protein containing mouse immunoglobulin-γ2a determinants, as evidenced by the immunocrossreactivity with the HRP-conjugated 2° reagent in the assay. In order to further characterize the biochemical properties of the secreted molecule, and thereby more firmly establish its identity, we analyzed the secreted protein by SDS-PAGE following immunoprecipitation of metabolically labelled proteins from ELISA positive cell lines.

For this analysis, two ELISA positive cell lines were selected at random, and cells arising from the primary transfection were expanded into 10 ml cultures for metabolic labelling of proteins by incubation with $^{35}$S-methionine. The metabolic labelling and subsequent immunoprecipitation were carried out essentially as described in Harlow and Lane, (1988) in *Antibodies, A Laboratory Manual,* Cold Spring Harbor, N.Y. Briefly, one confluent plate each of cells (0.5–1×$10^7$ cells) from experimental (transfected) and control (untransfected) lines were harvested by centrifugation at 1000 rpm in a benchtop clinical centrifuge, per labelling reaction. The cell pellets were washed 2X with sterile 1X PBS (37° C.), 1X with methionine free media (37° C.), and then resuspended in 1 ml each of methionine free media (Dulbecos Modified Eagle Medium, without L-methionine, without L-glutamine, GIBCO) supplemented with dialyzed 10% fetal calf serum (FCS, Hyclone), and 2 mM glutamine. The cells were incubated at 37° C. for 30–45 minutes to deplete endogenous methionine pools. Protein labelling was then carried out by addition of 100–200 μCi of $^{35}$S-methionine (Amersham, ≧1,000 Ci/mmol), and a further incubation of the cultures at 37° C. for 5–7 h. The metabolically labelled cells were harvested as described above, and the supernatant fractions saved for analysis of secreted proteins by immunoprecipitation as described below. In order to analyze intracellular synthesis, the cells were lysed by resuspending the cell pellets in 0.9 ml ice cold Tris buffered saline (TBS, 50 mM tris-Cl, pH 7.5, 150 mM NaCl), and lysed immediately by addition of 5% nonidet-P40 (NP40) to 0.5% final concentration. The protease inhibitor, phenylmethylsulonyl flouride (PMSF) was added to a final concentration of 1 mM, and the lysate(s) incubated on ice for 20 minutes. Cellular debris/insoluble material was removed from the cell lysate by centrifugation at 12,000 x g for 10 minutes at 4° C. The supernatant from this step, containing cell lysate, was recovered and saved for further analysis.

Preliminary immunoprecipitations with this crude lysate and supernatant fractions revealed a high level of background, presumably from non-specific adsorption of metabolically labelled proteins to the antibody conjugated agarose beads employed in the experiment. Hence, these two fractions were routinely pre-cleared by overnight adsorption to a rabbit IgG-agarose beads (Sigma, 100 μl beads/ml lysate or supernatant), which served as a non-specific adsorbent. The cleared supernatants were recovered following a brief centrifugation to remove the non-specific adsorbent, and used in subsequent immunoprecipitation experiments described below.

Immunoprecipitations of radiolabelled protein were carried with 100 μl aliquots from pre-cleared cell lysates and supernatants prepared as described above. The samples were immunoprecipitated directly with both rabbit IgG-agarose and protein-A agarose, using 5 μl protein conjugated agarose resin/100 μl sample, at 4° C. for 1–3 hours with constant agitation using a TOMY micro tube mixer. Alternatively, the samples were also immunoprecipitated in a two step procedure using a purified 1° antibody (1 μl/100 μl sample) at 0°–4° C. for 1–3 hrs, followed by protein A-agarose as described above. The samples were then prepared for washing by a brief centrifugation at 12,000g for 15–30 seconds. The radioactive supernatant was removed by aspiration. The immunecomplex coated agarose beads were washed 3X with 1 ml/wash of a solution containing 0.5% NP-40, 0.2% sodium deoxycholate, and 0.1% SDS in 1X TBS (NDS solution), followed by a final wash with 1X TBS (to remove detergents). The immune complex coated agarose beads were air dried overnight at room temperature prior to SDS-PAGE analysis of the immunoprecipitated product.

For polyacrylamide gel analysis of the immunoprecipitated products, the samples were resolubilized in Laemmli sample buffer (2% SDS, 10% glycerol, 10 mM DTT (dithiothreitol), and 60 mM Tris-Cl pH 6.8) in a boiling H$_2$O bath for 10 minutes. For analysis on non-reducing gels, the samples were resolubilized in Laemmli buffer minus DTT. Aliquots of the resolubilized samples were then loaded onto 10% or 12% polyacrylamide gels containing 0.1% SDS prepared and run according to the method of Laemmli, (1970) *Nature* 277:680–688 described in Harlow and Lane, (1988) in *Antibodies, A Laboratory Manual,* Cold Spring Harbor, N.Y. Two-dimensional gel analysis of the samples was carried out essentially as described in O'Farrell (1975) *J. Biol. Chem.* 250:4007–4021. Analytical experiments using broad pI range test IEF gels established the pI of the immunoprecipitated protein was in the neutral pH range. Consequent fine pI range titration further established a pH range in the IEF gels of 6–8 as optimal for maximal resolution of the proteins isoforms. Hence, the isoelectric focusing gels contained 2% (vol/vol) ampholytes pH range 4–10, and 4% (vol/vol) pH 6–8 ampholytes (BioRad). Following electrophoresis, gels were fluorographed, dried, and the results visualized by autoradiography.

Immunoprecipitation of cell lysates or supernatants with protein-A agarose revealed the exclusive presence of a major polypeptide band of 68 kD apparent molecular weight in both the intracellular and supernatant fractions of material from transfected cells, and its complete absence from untransfected cells. A protein of identical molecular weight is also immunoprecipitated with a two step procedure using either affinity purified goat anti-mouse IgGγ (GαmIgγ) as the 1° antibody followed by protein A-agarose, or goat anti-human κ (GαHuκ) as the 1° antibody followed by protein A-agarose.

Hence, the immunoprecipitation data confirmed the secreted expression by transfected cells only (25-1, as well as Sp2/0), of a protein bearing mouse IgGγ2a determinants. The data furthermore extend the observations from ELISA assay and document the intracellular expression of this protein by transfected cells only. The apparent molecular weight of this protein, 68 kD, agrees favorably with its predicted molecular weight, 54 kD, based on knowledge of its predicted primary structure. The 14 kD difference can be accounted for by post-translational modifications, e.g. glycosylation, which are known to occur on antibody molecules. A major site for N-linked glycosylation is in the CH2 domain of the molecule, which is retained in our chimeric construct.

A second major conclusion from the one-dimensional SDS-PAGE analysis of immunoprecipitated products is that the putative chimeric β-TCR/γ2a protein, a chimeric Ig heavy chain, is expressed in the absence of any requirement for assembly with light chain prior to its secretion from the cell. This is evidenced by two observations. The first observation is that immunoprecipitation of radiolabelled proteins from transfected 25-1 cells by either protein A-agarose alone or with Gαmγ followed by protein A-agarose failed to co-immunoprecipitate a polypeptide in the known size range of Ig light chains (~25 kD). The cell line 25-1 was derived from Sp2/0 by transfecting it with a humanized anti-TAC κ light chain construct. Thus, it is expressing high levels of a humanized κ light chain. The second, and more conclusive piece of evidence in support of the notion that the chimeric β-TCR/γ2a heavy chain is secreted in the absence of any requirement of prior assembly with a light chain, is its expression in Sp2/0 cells. Sp2/0 cells do not secrete any endogenous light chain, yet this protein is immunoprecipitated from both lysate and supernatants of transfected cells only, by either protein A-agarose alone, or Gαmγ followed by protein A-agarose.

3. The Putative Chimeric β-TCR/γ2a Heavy Chain is Secreted as a Homodimer.

The hinge domain in antibody molecules contains two important cysteine residues which are responsible for inter-chain disulfide linkages between immunoglobulin heavy chains. The formation of these interchain disulfide bonds is important to the structural integrity of native antibody molecules. We were interested in determining whether these sites would retain their native properties, i.e. serving to cross-link heavy chain monomers into dimers by disulfide linkages, in the chimeric molecules encoded by our construct. Thus, in order to obtain information regarding the quarternary structure of the protein, we analyzed its electrophoretic properties under nonreducing conditions.

For this analysis, radiolabelled proteins from transfected and untransfected cells were immunoprecipitated as described. Subsequent to drying, the immunoprecipitated products were resolubilized in Laemmli buffer lacking the reducing agent DTT. The solubilized immunoprecipitated products were analyzed by SDS-PAGE on 6% polyacrylamide gels. The pattern of immunoprecipitated products is similar to that observed earlier. Both protein A-agarose alone, and GαmIgγ followed by protein A-agarose, specifically immunoprecipitate a readily detectable product from transfected cell lysates and supernatants. A major difference, however, between the results observed in the absence of reducing agent compared with those in the presence of reducing agent is in the apparent molecular weight of the immunoprecipitated products. The apparent molecular weight of the immunoprecipitated product under reducing conditions (where both intra- and inter-chain disulfide bonds are reduced) was 68 kD. Under non-reducing conditions, the mobility of this protein in the supernatant fraction, shifts to approximately 110 kD.

Immunoprecipitation of the intracellular fraction revealed a doublet of bands, both of higher apparent molecular weight than observed under reducing conditions. One of these two bands is of similar apparent molecular weight as that observed in the supernatant fraction. The second band is ~96 kD apparent molecular weight. One explanation, given that it is present only in the intracellular fraction of transfected cells, is that it corresponds to an unglycosylated form of the putative chimeric β-TCR heavy chain. The plausibility of this explanation arises from two facts. First is that the sites for N-linked glycosylation in the CH2 domain are contained within the chimeric molecule. Second, glycosylation was demonstrated to occur indeed and required for the secreted expression of a chimeric VαCκ light chain Mariuzza and Winter, (1989) *J. Biol. Chem.* 264:7310-7316. Thus, the apparent molecular weight of the nonreduced, presumably unglycosylated protein, is approximately double its predicted molecular weight of 54 kD derived from its primary structure.

Therefore, the data from analysis of immunoprecipitated products under non-reducing conditions established that the chimeric TCR/heavy chain is cross-linked via disulfide linkages to form a homodimer. Although we do not have direct evidence, the most probable site for this is cross-linking is via the Cys residues encoded in the hinge domain of the Ig portion of the molecule.

4. The Chimeric Protein Secreted from Cells Transfected with pVβ8.1(Δtm)-γ2a(ΔCH1) Contains β-TCR Determinants.

A commercially available antibody that crossreacts with common determinants on human β-TCR chains, βF1 (T-Cell Sciences), was used to demonstrate, by western blot analysis, the presence of human β-TCR determinants on the chimeric protein secreted by transfected cells. For this analysis, a 25-1 primary cell line expressing the putative chimeric β-TCR/heavy chain protein was cloned by limiting dilution. Cell lines expressing higher levels of the chimeric protein, as assayed by the ELISA method described above, were identified. One of these was expanded further and used as a source for preparative isolation of chimeric β-TCR from large scale tissue culture supernatants.

For purification of preparative amounts of the protein, the clonal cell line was first acclimatized to growth under serum-free media conditions. Acclimatization to serum free media conditions was carried out initially on a gradual basis over the course of approximately 7-10 days. A dense 10 ml culture of cells (~$10^6$ cells) growing in DME-High Glucose media (Irvine Scientific) supplemented with 10% FCS was passaged daily by splitting the plate 1→2, and fed with DME-High Glucose media supplemented with 1% Nutridoma NS (Boehringer Mannheim), such that the vol/vol ratio of the final media after feeding increased from 9.0% FCS supplemented media/0.10% Nutridoma supplemented media on day one following the initial split, to 0% FCS supplemented media/1% Nutridoma supplemented media at the end. Once a cell culture had been established and reached a vigorous growth state in serum free media, the culture was expanded to preparative scale for isolation of the chimeric β-TCR. Initially, 0.5-0.6 liter cell cultures were employed as starting material. The cells were maintained in 1.0 l. flasks as 100 ml cultures for 2-5 days, and then harvested. Secreted proteins in the supernatants were then concentrated using an Amicon concentrator (model no 8200), and either PM10, PM30, or XM50 filtration membranes. The starting supernatants were concentrated to 15-20 ml final volume. The chimeric β-TCR protein was purified from this concentrated supernatant by a one-step affinity purification on a recombinant protein-A column (Repligen) essentially as described in Harlow and Lane, (1988) in *Antibodies. A Laboratory Manual*, Cold Spring Harbor, N.Y. Briefly, binding of the ligand to the column was achieved by two passages of the concentrate over the column, and the column was washed with 10 volumes of 1X PBS. The ligand was eluted from the column with 5 volumes of 50 mM Glycine (pH 2.5), 150 mM NaCl. The eluant was collected in 1 or 2 ml fractions (depending on the volume of the column), and the pH immediately raised to neutral by addition of a pre-titrated amount of 1M Tris-Cl (pH 9.0). The protein peak in the eluant was identified by $A_{280}$ measurement, which also served as an initial estimation of the yield of total protein.

The presence of β-TCR determinants in the putative chimeric protein were established by western blot analysis. For this experiment, 1-2 μg of total protein eluted from the protein-A column was loaded, following denaturation in reducing Laemmli buffer, onto a preparative well (1 mm × 8 mm × 4 mm), and electrophoresed into a 12% polyacrylamide gel. The proteins were then electrophoretically transferred onto nitrocellulose membrane for 2-3 hours with a Transphor model TE-50 electroblotter (Hoeffer Scientific Instruments) as described in Harlow and Lane, (1988) in *Antibodies, A Laboratory Manual*, Cold Spring Harbor, N.Y. Following transfer, the membrane was marked to assign polarity with respect to the original gel, and then mounted in a PR150 mighty small deca probe western blot staining apparatus (Hoeffer Scientific Instruments), and incubated in 2-3 ml/lane of 3% BSA, 1X PBS for 1 h at room temperature to block non-specific protein binding sites on the membrane. The presence of β-TCR determinants in the affinity purified secreted protein from transfected cells was documented using a three-step reagent system. The reagents were: 1°-100 X diluted βF1 MAb (overnight); 2°-biotin conjugated goat anti-mouse kappa (Fisher Biotech) affinity purified antibody (1-2 hr); and 3°-1000 X diluted alkaline phosphatase conjugated strepavidin (Sigma, ½-1 hr). All reagents were diluted in 1% BSA, IXTBS, 0.1% NaN3, and the blot washed between addition of subsequent reagents with 1X TBS, 0.1% Tween-20. Following the 3° reagent, the blot was washed with 1X TBS, and then incubated with alkaline phosphatase substrate (Nitro Blue Tetrazolium+5-Bromo-4-chloro-3-indoyl-phosphate, Sigma, as described in Harlow and Lane, Supra) to visualize antibody-antigen complex. In control experiments, it was established that the 3° reagent alone did not cross react with the test antigen when diluted at least 100X, and the 2° reagent plus 3° reagents alone did not cross react when the 2° reagent was diluted at least 1000X.

The results of this experiment established that at a 1000 X (or higher) dilution of the 2° reagent, an immuno-crossreactive product is observed only when the blot was incubated with the 1° reagent, βF1. Furthermore, the apparent molecular weight of this product, 68 kD, agrees precisely with that of the protein-A immunoprecipitated products described above. Therefore, this data established the presence of β-TCR determinants in the secreted product expressed by the transfected cell lines.

The purity of these affinity purified protein preparations was assessed by quantitative one and two-dimensional SDS-PAGE, and by these criteria, typical purity of the chimeric β-TCR from batch to batch varied between 95-99%. The major contaminant between batches was usually the humanized κ-light chain (migrating at ~20 kD apparent molecular weight), which is also expressed by the transfected cell line used for the purification of the chimeric β-TCR.

The purity of chimeric β-TCR batches was assessed by silver-staining of one-dimensional SDS-PAGE. Silver staining was carried out using a kit from Stratagene, and the instruction provided by the manufacturer. This analysis revealed the presence of a major polypeptide band of 68 kD apparent molecular weight as the primary elution product from the protein-A column. This corresponds precisely with the size of the polypeptide immunoprecipitated by protein-A agarose, as well as the βF1 immuno-cross reactive product, in the experiments described above. (A faint band constituting 1-5% of the total yield was detectable in the 20 kD size range. This corresponded to the humanized κ light chain). This data established that a 68 kD protein is the predominant constituent in affinity purified protein from supernatant derived from transfected cells, and in conjunction with the evidence described above, this molecule bears both T-cell receptor, and immunoglobulin heavy chain determinants.

A more critical assessment of the purity of a protein preparation is its electrophoretic profile on two-dimensional SDS-gels (Harlow and Lane, (1988) in *Antibodies, A Laboratory Manual,* Cold Spring Harbor, N.Y.). Thus, in order to further characterize the protein heterogeneity of the 68 kD polypeptide band observed in the one dimensional gels, we analyzed the affinity purified protein preparation by two dimensional SDS-PAGE. In the interest of brevity, the results of this analysis will only be summarized here, as they simply confirmed the conclusions discussed above. Two-dimensional analysis of the affinity purified chimeric Vbβ.1/mouse γ2a protein revealed it to be comprised of at-least 6 isoforms, all of which had the same apparent molecular weight, and differed in their isoelectric points. The pI of the chimeric protein isoforms ranged from pH 7-7.5. Furthermore, all the isoforms of the affinity purified chimeric protein also posessed β TCR determinants by virture of their cross-reactivity to the βF1 antibody in a western blot analysis.

We conclude, therefore, that all the isoelectric variants observed in the affinity purified chimeric protein contain both immunoglobulin heavy chain determinants, as well as β-TCR determinants. Possible contributors to the iso-electric heterogeneity of immunoglobulin molecules which have been documented include post-translational modifications e.g. glycosylation (Williamson, (1978) in *Handbook of Experimental Immunology* (D. M. Weir, ed.), pp 9.1-9.31, Blackwell Scientific Publishers, Oxford, England). This is consistent with evidence presented earlier regarding the difference between predicted and apparent molecular weight of the chimeric protein, and the observation of a lower molecular weight form exclusively in the intracellular fraction when analyzed by non-reducing SDS-PAGE.

5. Evidence That The Chimeric β-TCR/Heavy Chain Protein is Vβ8.1 in its T-cell receptor domain.

The immuno-crossreactive data described above provide very convincing evidence that the protein secreted from cells transfected with the pVβ8.1 construct contains both β T-cell receptor determinants, and immunoglobulin heavy chain determinants, as expected. In order to obtain direct evidence of this fact, and to provide final verification of the identity of the chimeric protein as Vβ8.1 specific, we subjected the purified protein to N-terminal amino acid sequence analysis.

Accordingly, 18 μg/~260 pmoles of affinity purified chimeric protein, isolated as described above, were concentrated further by overnight precipitation at 4° C. in 5% trichloroacetic Acid (TCA). The precipitated protein was concentrated by centrifugation at 12,000 X g, washed 2 X with 90% ethanol, and dried in a speed-vac concentrator. The pellet was mailed to Dr. Richard Cook's lab in the Department of Microbiology and Immunology at the Baylor College of Medicine in Houston, Tex. for amino acid sequence analysis. The results from the sequenator were communicated to us by Dr. Cook, and are summarized in FIG. 5, which shows a comparison of the predicted amino acid sequence of Vβ8.1 deduced from the cDNA sequence, and the amino-terminal sequence determined from the affinity purified chimeric β-TCR protein. Amino acid residues whose identity could not be ascribed with 100% confidence by Dr. Cook are indicated in parentheses in FIG. 5. The sequence of the purified protein agrees exactly with the predicted sequence of Vβ8.1 for the first 10 residues sequenced (residues #2-11), and for 12 of the 14 residues sequenced. The identity of the first residue, gly, although in agreement with the predicted sequence, cannot be ascribed with confidence due to a technical limitation (Dr. Cook, personal communication).

The yield per residue at each cycle of the sequenator is a critical parameter in protein sequence determination. The magnitude of this parameter is useful in ascribing the degree of confidence to the sequence obtained as originating from the major/sole polypeptide in the preparation as opposed to originating from a minor contaminant in the protein preparation (due to e.g. a blocked amino-terminus of the major constituent). Typically this value is highest for the first few cycles, and drops at each progressive cycle thereafter, for technical reasons. The yield per residue for the first two amino acids determined (V and I), was 122 pmoles, and 130 pmoles, respectively. Based on the estimated initial amount of protein submitted for sequence analysis, 260 pmoles, this represents a yield per residue of 45-50%. Hence, we can be confident that the sequence determined was from the major polypeptide in the preparation, as opposed to a minor contaminant in the preparation.

The results from sequence analysis show that the amino-terminus of the purified protein expressed by the transfected cells agrees precisely for the first 10 residues, with that of Vβ8.1, starting 1 residue downstream of the predicted leader peptide cleavage site. This evidence establishes two important facts. First, the identity of the chimeric β-TCR/immunoglobulin heavy chain can be assigned positively and unambiguously as Vβ8.1 in its T-cell receptor domain. Second, it shows that the β-TCR leader peptide is correctly processed in myeloma cells, a heterologous cell line.

Therefore, we conclude that myeloma cells transfected with pCMVβ8.1(ΔTM)-γ2a(ΔCH1) express a soluble protein which is a chimeric Vβ8.1/mouse γ2a molecule into the extracellular media.

6. Generation of Monoclonal Antibodies Capable of Binding Native Determinants on T-Cell Surfaces from Mice Immunized With a Solubilized Chimeric Vβ8.1/mouse γ2a Protein.

Monoclonal antibodies to Vβ8.1 were generated using standard procedures (Kohler and Milstein, (1975) *Nature* 256:495–497; Harlow and Lane, (1988) in *Antibodies, A Laboratory Manual*, Cold Spring Harbor, N.Y.) by immunizing BALB/C mice with the chimeric Vβ8.1/mouse γ2a protein. Briefly, three mice were immunized according to the schedule presented in Table 2 below, and their spleens removed for fusion. Immunizations were performed using 5–10 µg of affinity purified chimeric Vβ8.1/mouse γ2a protein. The primary immunizations were with antigen in complete Freund's adjuvant, and subsequent boosts were with antigen in incomplete Freund's adjuvant. All injections were intraperitoneal, and all mice received a final boost three days prior to removal of spleens for cell fusions. Spleenocytes were processed for fusion with P3X cells, which were the fusion partners employed. Spleenocyte-myeloma fused hybridoma cell lines were selected in HAT media and supernatants from surviving colonies were tested for anti-Vβ8.1 antibodies by ELISA assay as described below.

TABLE 2

Immunization Schedule. Time between primary immunization and subsequent boosts is expressed as Δ(d).

| Mouse # | 1st boost | 2nd boost | 3rd boost |
|---------|-----------|-----------|-----------|
| 1 | 14 d | 7 d | NA |
| 2 | 14 d | 17 d | 42 d |
| 3 | 14 d | 17 d | NA |

Anti-Vβ8.1 antibody producing hybridoma cell lines were identified by a two step screen. The first involved an ELISA assay of cell supernatants. For this assay, ELISA plates were coated with 100 µl/well of affinity purified chimeric Vβ8.1/mouse γ2a protein at a concentration of 1.5 µg/ml (diluted in 1X PBS) for at-least 3 d at 4oC. The plates were then blocked for at-least 24 h with 200 µl/well of ELISA buffer. Following washing with 1X PBS, 0.1% Tween-20, test antibodies (i.e., supernatant from resistant hybridoma cells) were applied to the wells and the plates incubated at room temperature for at-least 2 hours. Next, the plates were incubated with 100 µl/well of 2000X diluted, biotin conjugated GαMIgκ (Fisher Biotech) for 1 h at room temperature. Finally, the plates were incubated with a 3° reagent, 200X diluted horseradish peroxidase conjugated strepavidin (Sigma) at room temperature for 30–60 minutes. The plates were washed in-between reagents with 3 changes of 1X PBS, 0.1% Tween-20, using 200 µl/well. Following the 3° reagent, the plates were washed 4X with 1X PBS alone. Positive samples were visualized by application of HRP substrate (Biorad).

Positive cell lines identified by the ELISA assay were expanded for determination of reactivity of the antibodies with native TCR determinants expressed on cell surface TCR β-chain by indirect immunoflourescence and quantified by flow cytometry using a FACScan (Becton Dickinson), reviewed in Parks et al., (1989) in *Fundamental Immunology* (W. E. Paul, ed.), Raven Press, New York). The specific β-TCR chain solubilized in this study (β8.1), is known to be expressed on the surface of the T-cell line Jurkat (Yanagai et al., (1984) *Nature* 308:145–149, Sangster et al., (1986) *J. Exp. Med.* 163:1491–1508). Consequently, supernatants from expanded Vβ8.1 positive ELISA hybridoma lines were tested for their ability to cross-react with native β-TCR epitopes by surface staining of Jurkat cells. Briefly, 3–5 X $10^5$ Jurkat cells (in 100 µl 1X PBS, 0.01% sodium azide) were incubated with hybridoma supernatant in 96-well micotitre plates, at 0°–4° C. for 30 min. The cells were washed 1X with 250 µl/well PBS/azide, and incubated with 25 µl/well FITC conjugated Gα-MIgG for another 30 minutes as above. Following a final wash, the cells were fixed by resuspending in 1% paraformaldehyde, and analysed by FACS scan.

The level of background/non-specific staining (control) was established using media alone, and positive controls for staining intensity employed included the following 3 antibodies: OKT3 (Ortho diagnostic), WT31 (sold as TCR-1, Becton-Dickinson), αVβ8 (T-cell Sciences), and W6-32 (ATCC). Respectively, these antibodies recognize the CD3 complex on T-cells, a shared conformational epitope between CD3 and α/β TCR (Van de Griend, et al., (1988) *J. Immunol.* 140:1107–1110), Vβ8 chain of the T-cell receptor (Tian, W-T et al., (1989) FASEB J. 3:A486 abstracts), and a Class II MHC determinant (*J. Immunol.* (1982) 128:129–135). Various of the monoclonal antibodies produced as described above stained positively the Jurkat cells, indicating they bind to the Vβ8.1 chain on the cell surface.

Although the present invention has been described in some detail by way of illustration and example for purposes of clarity and understanding, it will be apparent that certain changes and modifications may be practiced within the scope of the claims.

What is claimed is:

1. A soluble polypeptide comprising X1-V$_\beta$-C$_\beta$-X2-CH2-CH3, wherein
   V$_\beta$ is a variable region domain of a human T-cell receptor β chain;
   C$_\beta$ is a constant region domain of a human T-cell receptor β chain in which transmembrane and intracellular segments are deleted;
   CH2 is a heavy chain constant region encoded by the CH2 region of an immunoglobulin gene;
   CH3 is a heavy chain constant region encoded by the CH3 region of an immunoglobulin gene;
   X1, if present, comprises a leader peptide and
   X2, if present, comprises an immunoglobulin Hinge region.

2. A polypeptide of claim 1, wherein the variable region domain is selected from the group of subfamilies V$_{\beta}$21-V$_{\beta}$220.

3. A polypeptide of claim 1, wherein at least one of the heavy chain constant regions is from a mouse.

4. A polypeptide of claim 1, wherein the polypeptide is soluble in an aqueous buffer.

5. A polypeptide of claim 1, wherein the V$_\beta$ is the V$_\beta$ 8.1 T-cell receptor chain.

6. A polypeptide comprising human T-cell receptor V$_\beta$-C$_\beta$ domains fused to mouse immunoglobulin CH2-CH3 domains, without a complete CH1 domain, wherein the polypeptide is soluble.

* * * * *

UNITED STATES PATENT AND TRADEMARK OFFICE
CERTIFICATE OF CORRECTION

PATENT NO. : 5,216,132
DATED : June 1, 1993
INVENTOR(S) : GURIQBAL S. BASI

It is certified that error appears in the above-indentified patent and that said Letters Patent is hereby corrected as shown below:

Col. 26, L. 53, please change "$V_{62}1-V_{62}20$" to read --$V_\beta 1-V_\beta 20$--.

Signed and Sealed this

Twenty-second Day of March, 1994

Attest:

BRUCE LEHMAN

Attesting Officer

Commissioner of Patents and Trademarks